US00PP16466P2

(12) United States Plant Patent
Olesen

(10) Patent No.: US PP16,466 P2
(45) Date of Patent: Apr. 18, 2006

(54) SHRUB ROSE PLANT NAMED 'POULTC005'

(50) Latin Name: ***Rosa* hybrid**
Varietal Denomination: Poultc005

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 79 days.

(21) Appl. No.: 11/002,356

(22) Filed: Dec. 1, 2004

(51) Int. Cl.
*A01H 5/00* (2006.01)

(52) U.S. Cl. ..... Plt./102

(58) Field of Classification Search ..... Plt./102, Plt./103, 104, 107

See application file for complete search history.

*Primary Examiner*—Anne Marie Grunberg
*Assistant Examiner*—June Hwu

(57) ABSTRACT

A new garden rose plant of the shrub class which has abundant, pink flowers and attractive foliage. This new and distinct variety has shown to be uniform and stable in the resulting generations from asexual propagation.

2 Drawing Sheets

Botanical classification: *Rosa* hybrid.
Variety denomination: 'Poultc005'.

SUMMARY OF THE INVENTION

The present invention constitutes a new and distinct variety of garden rose plant that originated from a controlled crossing between the female parent plant, an unnamed seedling, and the male pollen parent plant, an unnamed seedling. The two parents were crossed during the summer of 1997 and the resulting seeds were planted in a controlled environment in Fredensborg, Denmark. The new variety is named 'Poultc005'.

The new variety may be distinguished from its female parent, by the following combination of characteristics:

1. 'Poultc005' has a taller growth habit than the female parent plant.
2. 'Poultc005' exhibits flowers with a smaller diameter than those of the female parent.
3. Flowers of 'Poultc005' have fewer flower petals than those of the female parent.

The new variety may be distinguished from its pollen parent by the following combination of characteristics:

1. The pollen parent has darker pink flowers than those of 'Poultc005'.
2. The pollen parent plant has larger flowers than 'Poultc005'.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Disease resistance;
4. Suitability for growth in a container.

This combination of qualities is not present in previously available commercial cultivars of this type, known to the inventors, and distinguish 'Poultc005' from all other varieties of which we are aware.

As part of the rose development program, Mogens N. Olesen germinated the seeds from the aforementioned hybridization during winter of 1996 and conducted evaluations on the resulting seedlings in a controlled environment in Fredensborg, Denmark.

'Poultc005' was selected in the spring 1998 by the inventor as a single plant from the progeny of the aforementioned hybridization.

Asexual reproduction of 'Poultc005' by traditional budding and rooted cuttings was first done by Mogens N. Olesen in the nursery in Fredensborg, Denmark in July, 1998.

This initial and other subsequent asexual propagations conducted in controlled environments have demonstrated that the characteristics of 'Poultc005' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poultc005'. Specifically illustrated in the drawings are:

FIG. 1.1; Cluster of open flowers showing the attachment of leaves, buds, and receptacle;

FIG. 1.2; Mature leaves;

FIG. 2.1; Flower buds at various stages of development;

FIG. 2.2; Flower petals and petaloids, detached;

FIG. 2.3; Sepals, receptacle, and peduncle;

FIG. 2.4; Stem exhibiting thorns.

DETAILED DESCRIPTION OF THE VARIETY

The following is a description of 'Poultc005', as observed in its growth in a field nursery in Jackson County, Oreg. Observed plants are 3 years of age, grown on *Rosa multiflora* understock. Color references are made using The Royal Horticultural Society (London, England) Colour Chart, 1995, except where common terms of color are used.

For a comparison, several physical characteristics of the rose variety 'Poulor', a rose variety from the same inventors described and illustrated in U.S. Plant Pat. No. 12,511 dated Apr. 2, 2002, are compared to 'Poultc005' in Chart 1.

CHART 1

| | 'Poultc005' | 'Poulor' |
|---|---|---|
| Sepal outer surface color | Yellow-Green Group 146A to 146B. | Green Group 143C. |
| Bud form | Ovate. | Short, pointed ovoid. |
| General tonality | Red-Purple Group 67D to Red Group 55D. | Red-Purple Group 65A. |

FLOWER AND FLOWER BUD

Blooming habit: Continuous.

Flower bud:

*Size.*—Upon opening, 23 mm in length from base of receptacle to end of bud. Diameter is 11 mm.

*Bud form.*—Ovate.

*Bud color.*—As sepals unfold, petals are Red Group 48D with basal intonations which are Yellow-White Group 158C to Green-White Group 157B. Sepal Upper Surface: Color: Yellow-Green Group 147C. Surface: Weakly pubescent. Sepal Lower Surface: Color: Yellow-Green Group 146A to 146B. Texture: Smooth. Sepal Shape: Sepal apex is cirrhose. Base is flat at union with receptacle. Sepal Margin: Margins have weak foliaceous appendages on three of the five sepals. Size: 25 mm (l)×8 mm (w).

*Receptacle.*—Surface: Smooth. Shape: Urn-shaped. Size: 7 mm (h)×6 mm (w). Color: Yellow-Green Group 146C.

*Pedicel.*—Surface: Rough with many small prickles and stipitate glands in numerous quantity. Length: 25 mm average length. Diameter: 2 mm on average. Color: Yellow-Green Group 144A with strong anthocyanic pigments the color of Greyed-Orange Group 184A observed. Strength: Strong strength.

*Borne.*—In clusters or cymes with 3 to 6 flowers per stem.

Flower bloom:

*Fragrance.*—None.

*Duration.*—The blooms have a duration on the plant of approximately 7 to 10 days. Afterwards, petals fall cleanly away from plant.

*Size.*—Flower diameter is 45 to 50 mm when open. Depth is 25 mm.

*Form.*—General shape is an open cup with petals that curve out from the center.

Shape of flower when viewed from the side:

*Upon opening, upper part.*—Flat.

*Upon opening, lower part.*—Flat.

*Open flower, upper part.*—Flattened convex.

*Open flower, lower parts.*—Concave.

Petalage: 19 petals under normal conditions, 5 of which are petaloids.

Flower color:

Upon opening, petals:

*Outermost petals.*—Upper surface: Red Group 55D blending with Yellow-White Group 158D at basal zone. Darker colored veins of Red Group 55A observed. Lower surface: Red Group 55C to Red Group 48D at marginal and middle zones, blending with Yellow-White Group 158A at the basal zone. Occasional streaks of Yellow-White Group 158A and Yellow Group 6C and 6D extend to marginal zone.

*Innermost petals.*—Upper surface: Red Group 55D blending with Yellow-White Group 158D at basal zone. Darker colored veins of Red Group 55A observed. Lower surface: Red Group 55C to Red Group 48D at marginal and middle zones, blending with Yellow-White Group 158A at the basal zone. Occasional streaks of Yellow-White Group 158A and Yellow Group 6C and 6D extend to marginal zone.

Upon opening, basal petal spots:

*Outermost petals.*—Upper surface: Yellow Group 6C. Lower surface: Yellow Group 6C.

*Innermost petals.*—Upper surface: Yellow Group 4B. Lower surface: Yellow Group 4B.

After opening, petals:

*Outermost petals.*—Upper surface: Red Group 55D blending with Yellow-White Group 158D at basal zone. Darker colored veins of Red Group 55A observed. Lower surface: Red Group 55C to Red Group 48D at marginal and middle zones, blending with Yellow-White Group 158A at the basal zone. Occasional streaks of Yellow-White Group 158A and Yellow Group 6C and 6D extend to marginal zone.

*Innermost petals.*—Upper surface: Red Group 55D blending with Yellow-White Group 158D at basal zone. Darker colored veins of Red Group 55A observed. Lower surface: Red Group 55C to Red Group 48D at marginal and middle zones, blending with Yellow-White Group 158A at the basal zone. Occasional streaks of Yellow-White Group 158A and Yellow Group 6C and 6D extend to marginal zone.

After opening, basal petal spots: Upper surface: Yellow Group 6C. Lower surface: Yellow Group 6C.

*Innermost petals.*—Upper surface: Yellow Group 6C. Lower surface: Yellow Group 6C.

General tonality: On open flower Red-Purple Group 67D to Red Group 55D. No change in the general tonality at the end of the 10th day. Afterwards petals turn to White Group 155A with light intonations of Red Group 55D.

Petals:

*Petal reflex.*—Somewhat reflexed.

*Margin.*—Entire and uniform.

*Shape.*—Apex: Rounded. Base: Acute.

*Size.*—26 mm (l)×23 mm (w).

*Texture.*—Smooth.

*Thickness.*—Thin.

*Arrangement.*—Not Formal.

Petaloids:

*Quantity.*—Normally 5.

*Color.*—Upper Surface: Red-Purple Group 67D with basal spot Yellow Group 6C. Lower Surface: Red Group 55D with basal spot Yellow Group 6C.

*Size.*—8 mm (l)×6 mm (w).

Reproductive organs:

*Pistils.*—Length: 4 mm. Quantity: 30 to 40.

*Pollen.*—None observed.

*Anthers.*—Size: 3 mm in length. Color: Greyed-Orange Group 163B. Quantity: 80 to 85.

*Filaments.*—Color: Yellow Group 2C. Length: 5 mm.

*Stigmas.*—Inferior in location, relative to the length of the filaments and the height of the anthers. Color: Yellow-White Group 158A.

*Styles.*—Color: Red-Purple Group 61A.

*Hips.*—None Observed in the field nursery in Jackson County Oreg.

PLANT

Plant growth: Upright to bushy. When grown as a budded field grown plant on *Rosa multiflora* understock, the average height of the plant is 60 to 100 cm.

Stems:

*Color.*—Young wood: Yellow-Green Group 145A. Older wood: Yellow-Green Group 146C.

*Length.*—60 to 80 cm from the base of the plant to the flowering portion.

*Diameter.*—6 mm.

*Internodes.*—20 mm.

*Surface texture.*—Young wood: Smooth. Older wood: Smooth.

Thorns:

*Incidence.*—12 thorns per 10 cm of stem.

*Colors.*—Juvenile thorns: Greyed-Purple Group 184A.

*Adult thorns.*—Greyed-Orange 164B with intonation of Greyed-Orange 166B.

*Shape.*—Upper side: Concave. Lower side: Concave.

Plant foliage: 7 leaflets on normal leaves in the middle of the stem.

*Compound leaf size.*—On average, 100 mm (l)×60 mm (w).

*Average quantity.*—4 to 5 leaves per 10 cm of stem.

*Leaf color.*—Mature Foliage: Upper surface: Yellow-Green Group 147A. Lower surface: Yellow-Green Group 147B.

Plant leaves and leaflets:

*Stipules.*—Size: 17 mm. Margins: Finely serrated with few stipitate glands. Color: Yellow-Green Group 146A.

*Petiole.*—Length: 17 mm. Diameter: 1.5 mm. Upper surface: Color: Greyed-Red Group 182A. Lower surface: Color: Yellow-Green Group 144B. Observations: Rough texture, with few stipitate glands and small prickles.

*Rachis.*—Length: 45 to 50 mm. Above: Color: Yellow-Green Group 144A with Greyed-Red Group 182A. Underneath: Color: Yellow-Green Group 144B. Observations: Rough with few stipitate glands and small prickles.

*Leaflet.*—Size: Normally 37 mm (l)×26 mm (w). Edge: Serrated. Shape: Generally ovate. Base: Rounded. Apex: Cuspidate. Texture: Smooth. Thickness: Thick. Arrangement: Odd pinnate. Venation: Reticulate. Glossiness: Glossy.

Disease resistance: Above average resistance to powdery and downy mildews, rust, black spot, and *Botrytis* under normal growing conditions in Jackson County, Oreg.

Cold hardiness: The variety 'Poultc005' has been found to be cold tolerant to USDA Cold Hardiness Zone 6.

It is claimed:

1. A new and distinct variety of rose plant of the shrub rose class named 'Poultc005', described and substantially as illustrated herein, as a distinct and novel rose variety due to its abundant pink flowers, disease resistance, and extended period of bloom.

* * * * *

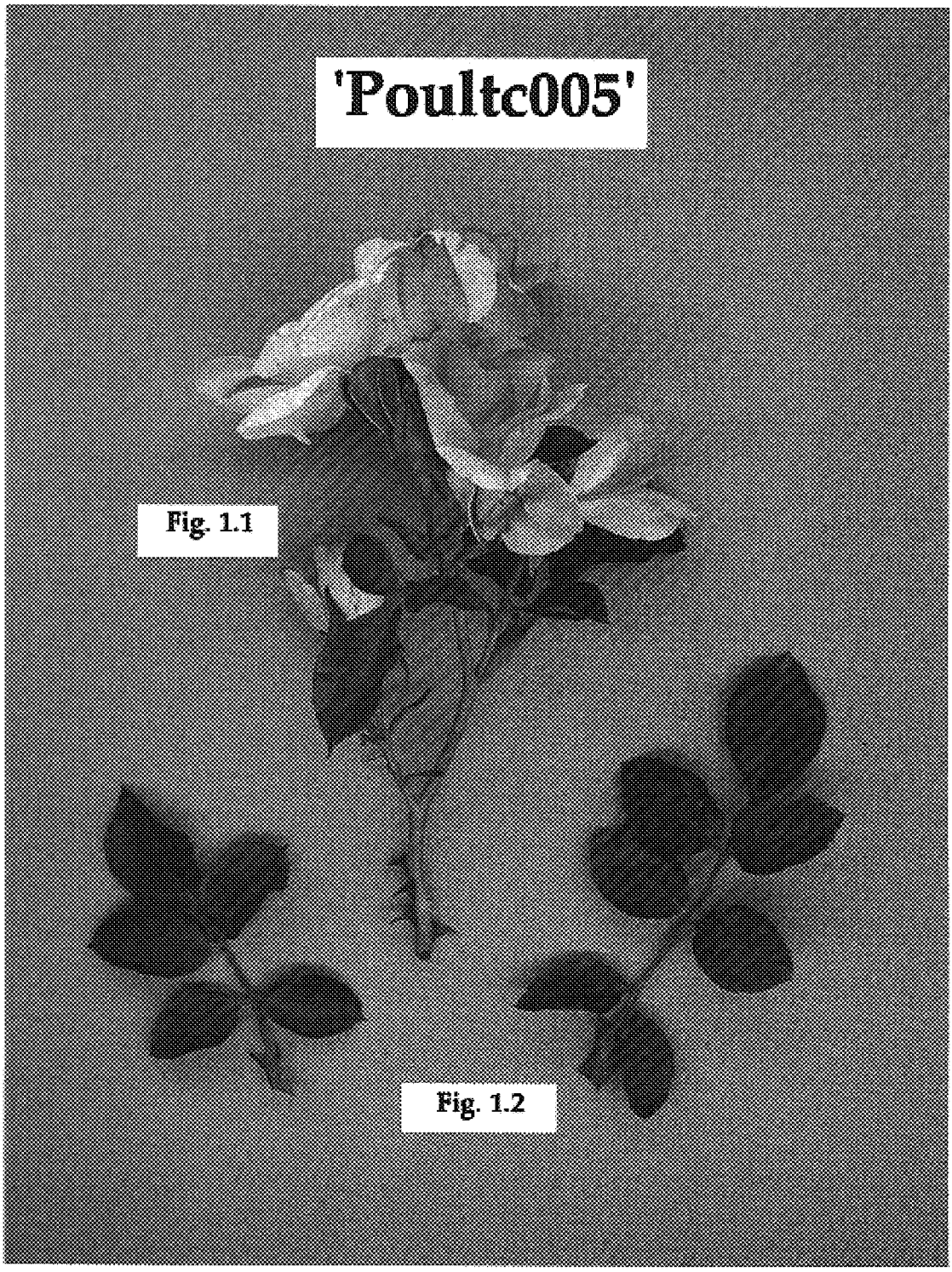
'Poultc005'
Fig. 1.1
Fig. 1.2

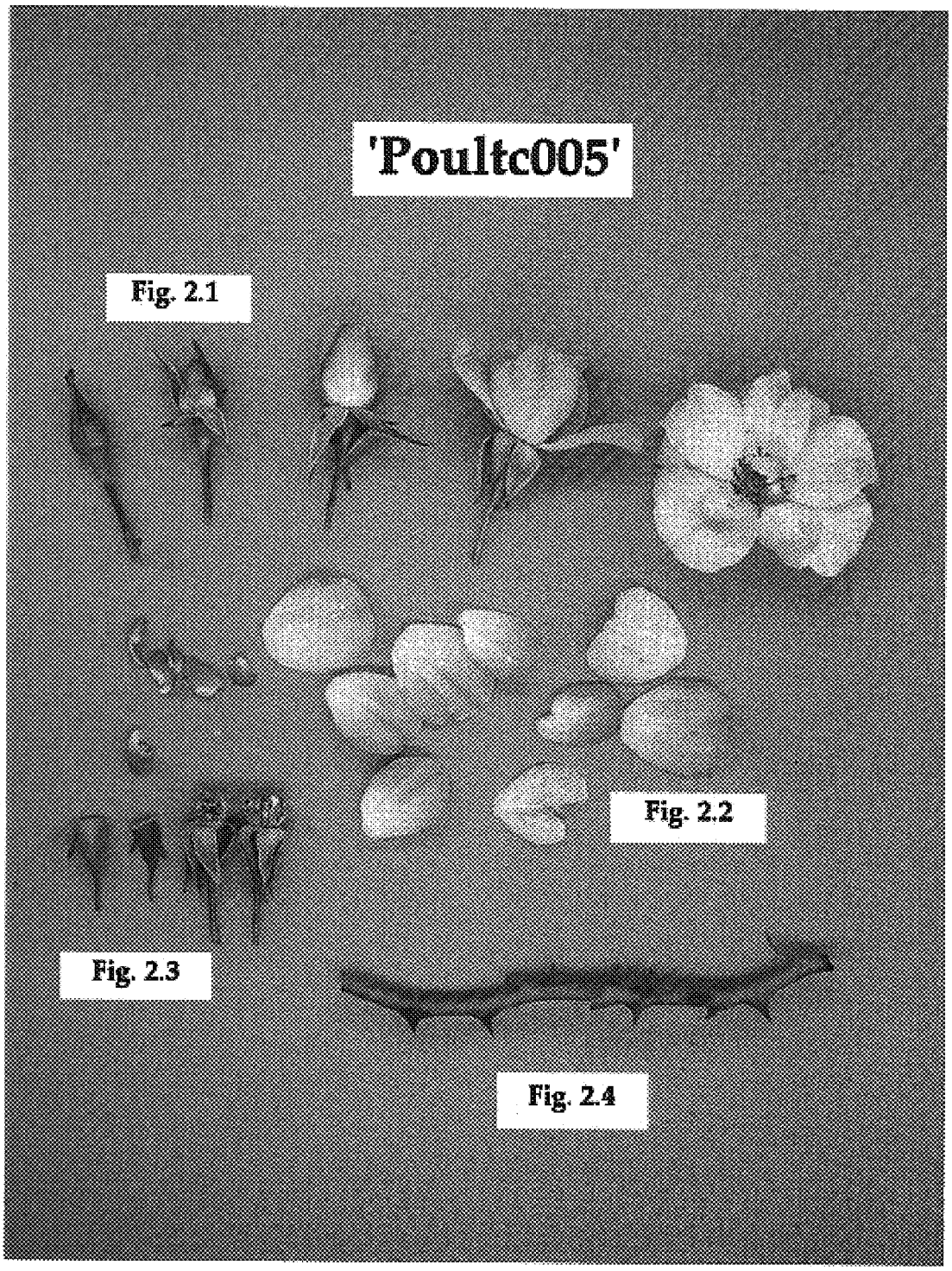
'Poultc005'
Fig. 2.1
Fig. 2.2
Fig. 2.3
Fig. 2.4